(12) United States Patent
Alder et al.

(10) Patent No.: US 7,686,311 B2
(45) Date of Patent: Mar. 30, 2010

(54) SYSTEMS, METHODS AND APPARATUS OF WHEELS FOR LATERAL MOTION OF MOBILE C-ARM X-RAY DEVICES

(75) Inventors: Samuel Lee Alder, Stansbury Park, UT (US); Vernon Thomas Jensen, Draper, UT (US)

(73) Assignee: General Electric Company, Schenectady, NY (US)

( * ) Notice: Subject to any disclaimer, the term of this patent is extended or adjusted under 35 U.S.C. 154(b) by 563 days.

(21) Appl. No.: 11/563,007

(22) Filed: Nov. 23, 2006

(65) Prior Publication Data

US 2008/0123818 A1 May 29, 2008

(51) Int. Cl.
*B62D 61/12* (2006.01)
(52) U.S. Cl. .................................... 280/43.23
(58) Field of Classification Search ............. 280/43.23, 280/43.17, 43, 638; 378/196, 197, 209, 195, 378/193; 180/199, 209
See application file for complete search history.

(56) References Cited

U.S. PATENT DOCUMENTS

| | | | | | |
|---|---|---|---|---|---|
| 1,774,700 | A | * | 9/1930 | Crane | 180/199 |
| 4,975,937 | A | * | 12/1990 | Horton et al. | 378/114 |
| 5,475,730 | A | * | 12/1995 | Galando | 378/157 |
| 5,835,557 | A | * | 11/1998 | Malmstrom | 378/197 |
| 5,901,200 | A | * | 5/1999 | Krause | 378/198 |
| RE36,415 | E | * | 11/1999 | McKenna | 378/4 |
| 6,095,685 | A | * | 8/2000 | Tamura | 378/196 |
| 6,105,977 | A | * | 8/2000 | Bengtsson et al. | 280/11.231 |
| 6,131,690 | A | * | 10/2000 | Galando et al. | 180/411 |
| 6,986,179 | B2 | * | 1/2006 | Varadharajulu et al. | 5/611 |

* cited by examiner

*Primary Examiner*—Frank B Vanaman
(74) *Attorney, Agent, or Firm*—Peter Vogel, Esq.; William Baxter, Esq.; Michael G. Smith, Esq.

(57) ABSTRACT

Systems, methods and apparatus are provided through which in some embodiments a lateral motion of an imaging device is provided by at least one friction reduction device that provides motion in a direction that is lateral to main wheels of the imaging device.

25 Claims, 17 Drawing Sheets

SYSTEMS, METHODS AND APPARATUS OF WHEELS FOR LATERAL MOTION OF MOBILE C-ARM X-RAY DEVICES

FIELD OF THE INVENTION

This invention relates generally to mobile imaging devices, and more particularly to the undercarriage of mobile C-arm X-ray devices.

BACKGROUND OF THE INVENTION

Mobile fluoroscopy "C-arm" systems are used in radiology departments and operating rooms (ORs) throughout the world. Quite often, the C-arm systems are required to be operated in different locations within a medical facility or different locations in a room. The C-arm systems are steered and maneuvered during transport from one location to another in mostly a "forward" direction. The C-arms are also maneuvered in lateral directions, such as a direction parallel to the OR table during patient imaging. Lateral directions are perpendicular to the "forward" direction.

Moving the C-arm systems laterally is very important in the use of the C-arm system. For example, when a patent is on the imaging table, the patient is in the lateral position because the C-arm is positioned over the patient. To perform a dye-contrast injection and follow the dye-contrast injection as the injected dye moves from the femoral artery down the leg and into peripheral vasculature, the C-arm must be moved accurately and swiftly along lateral directions.

One particular conventional C-arm design attempted to improve lateral movement of the C-arm system by providing limited lateral travel of the C-assembly with a lateral track at the top of the lift column, and locking the main wheels in the forward position. This design did not provide the amount of lateral travel needed for many common C-arm procedures, and compromised the stability of the C-arm system by shifting the weight from side to side over the base.

Most conventional C-arm systems accomplish lateral motion by rotating both main wheels 90 degrees, from the forward orientation to the lateral orientation. More specifically, the main wheels are mounted on the bottom of an undercarriage, and the undercarriage includes a rotating mount on the base. This method for lateral motion has served the industry for more than three decades, using design solutions for wheel rotation that range from a simple foot lever, to a more sophisticated handle-to-wheel rotational drive assembly. The main-wheel apparatus, however, complicates the design solutions for other features.

In particular, the main-wheel rotating undercarriage apparatus limits the size of the main-wheels, and ultimately limits the maximum weight of the C-arm system. The main wheels cannot be of large diameter in order to keep the main wheels from hitting the base while rotating the main wheels. Large main diameter wheels require a wider carriage in order to pivot the main wheels 90 degrees without running into the base of the C-arm system. However, a wider rotating carriage is not possible because the C-arms must be moved through doorways, and conventional C-arm systems are about as wide as possible for typical doorways. The main wheels cannot be of large width in order to reduce friction of the wheels on the floor while rotating the wheels. As a result, C-arm systems that have rotating wheels cannot be designed with a larger diameter main wheels or wider main wheels.

However, large main wheels are helpful, especially when the C-arm system is moved across carpeted floors. Carpeted floors are not uncommon in healthcare facilities, and are becoming increasingly common outside of sterile environments within the healthcare facilities.

Improved ease-of-transport and maneuverability continue to be high on the list of needed improvements. As mobile C-arm systems approach the equivalent functional features and image quality of fixed-room fluoroscopic X-ray systems, (counter to the goal of improved maneuverability), systems are becoming larger and heavier. Higher power X-ray generators, higher capacity X-ray tubes, and flat panel solid state X-ray detectors requiring on-board cooling solutions, all bring the mobile C-arm one step closer to state-of-the-art fixed-room system performance, but also increase the size, and significantly increases the weight. Rotating the main wheels underneath C-arm systems is becoming more and more difficult as the C-arm systems become heavier. The increasing weight of C-arm systems also indicates that moving the C-arm systems across carpeted floors will require larger wheels.

For the reasons stated above, and for other reasons stated below which will become apparent to those skilled in the art upon reading and understanding the present specification, there is a need in the art for an apparatus that configures mobile fluoroscopy C-arm systems (or other mobile imaging systems) for lateral movement and yet will accommodate large main wheels while not requiring a greater width of the C-arm system.

BRIEF DESCRIPTION OF THE INVENTION

The above-mentioned shortcomings, disadvantages and problems are addressed herein, which will be understood by reading and studying the following specification.

In one aspect, a mobile imaging system includes at least one wheel [known as lateral wheel(s) or known as secondary wheel(s)] that is mounted in the horizontal plane of the base of the mobile imaging system and perpendicular to the main wheels. When the lateral wheel(s) contacts the floor, at least some of the weight of the mobile imaging system is lessened on the main wheels, which in turn requires less force to move the mobile imaging system laterally. Rotating main wheel(s) is not required to configure the mobile imaging system for lateral movement, which in turn means that main wheels with a larger diameter can be installed on the mobile imaging system, and that a wide base is not required to accommodate a heavy base in order to accommodate a heavy mobile imaging system. Thus the need in the art is satisfied for an apparatus that more easily configures mobile fluoroscopy C-arm systems or other mobile imaging systems for lateral movement and yet will accommodate large main wheels while not requiring a greater width of the C-arm system. The wheel is one example of a friction reduction device.

In another aspect, an apparatus to image objects includes a base, one or more main wheel(s) mounted on the base of the apparatus, and one or more secondary wheels being mounted on the base, the secondary wheel(s) also being mounted in a perpendicular direction to the main wheels.

In yet another aspect, a mobile fluoroscopy C-arm system includes a base, and one or more main wheel(s) are mounted on the base. A plurality of castered wheels are mounted on the base and mounted forward of the one or more main wheel(s). One or more in-line wheel(s) are mounted on the base of the mobile fluoroscopy C-arm system and mounted rearward of the one or more main wheel(s) and mounted in a perpendicular direction to the one or more main wheel(s).

In still another aspect, a mobile fluoroscopy C-arm system includes a base. A plurality of main wheels are mounted on the base of the mobile fluoroscopy C-arm system. A plurality of castered wheels are mounted on the base of the mobile fluoroscopy C-arm system and mounted forward of the plurality of main wheels. One or more in-line wheel(s) are mounted on the base of the mobile fluoroscopy C-arm system and mounted in a perpendicular direction to the main wheels and in some embodiments are mounted rearward of the plurality of main wheels. A lift apparatus is operably coupled to the one or more in-line wheel(s) and operable to move the one or more in-line wheel(s) along a vertical axis of the mobile fluoroscopy C-arm system. A control mechanism is operably coupled to the lift motor to actuate and control the lift motor in movement of the in-line wheels. The control mechanism also includes an activate/deactivate switch that is operably coupled to the carriage mechanism to actuate and control the carriage mechanism in movement of the in-line wheel(s).

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into four sections. In the first section, a system level overview is described. In the second section, apparatus of embodiments are described. In the third section, embodiments of methods are described. Finally, in the fourth section, a conclusion of the detailed description is provided.

System Level Overview

Figure 1:
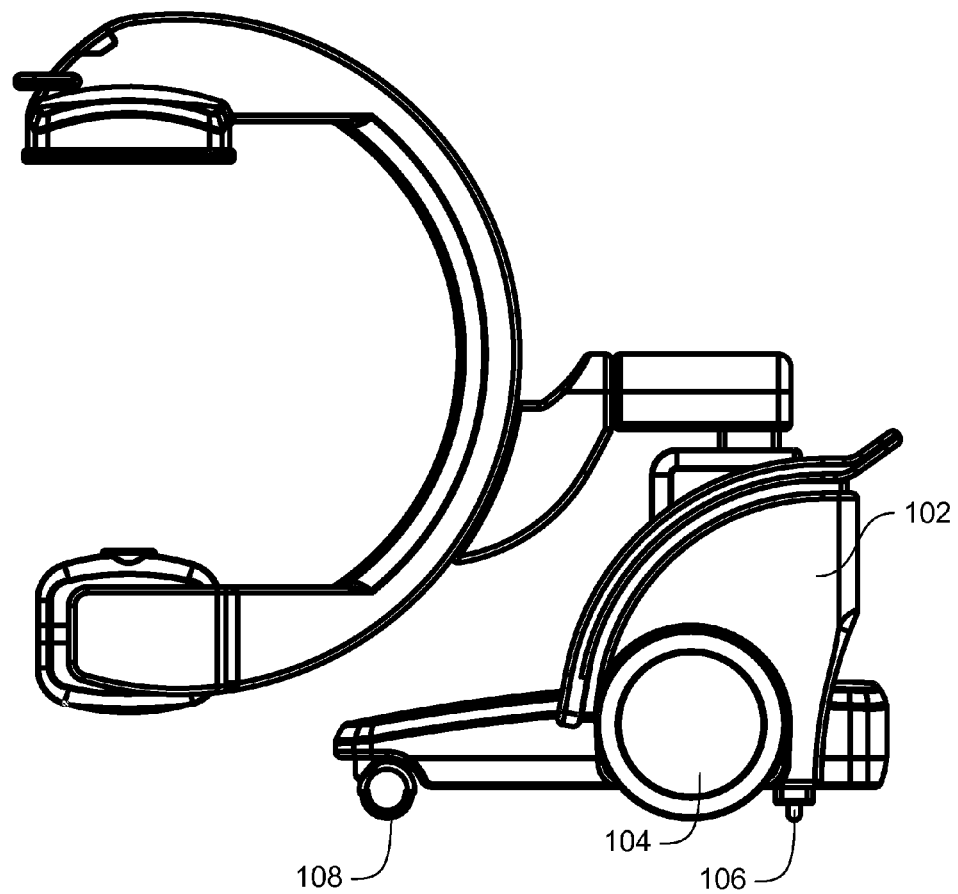
FIG. 1 is a side-view diagram of an overview of a system to image objects, according to an embodiment.

The system level overview of the operation of an embodiment is described in this section of the detailed description. FIG. 1 is a side-view diagram of an overview of a system to image objects, according to an embodiment. System 100 solves the need in the art for an apparatus that configures a mobile imaging system for lateral movement and yet will accommodate large main wheels while not requiring a greater width of the mobile imaging system.

System 100 includes a base 102 and a plurality of main wheels 104 mounted on the base 102. One example of a system 100 to image an object is a mobile fluoroscopy C-arm system.

System 100 also includes one or more secondary wheel(s) 106. The secondary wheel(s) 106 are mounted on the base 102. In some embodiments such as the embodiment shown in FIGS. 1, 3, 5, 7 the secondary wheel(s) 106 are also mounted rearward of the plurality of main wheels 104. The secondary wheel(s) 106 are mounted in a perpendicular or lateral direction to the main wheels.

Mounting the secondary wheel(s) 106 in a direction that is perpendicular or lateral to the main wheels 104 provides a means to move the system 100 in a lateral direction when the secondary wheel(s) 106 are in contact with the floor. As a result, the secondary wheel(s) 106 are often called lateral wheels.

Notably, the system 100 lacks rotating main wheels. The lack of a rotating main wheels reduces and possibly eliminates many limitations on the size of the main wheels 104 and eliminates or reduces the need for a wider apparatus, yet system 100, through the presence of the secondary wheel(s) 106, provides a means to configure the system 100 to be moved laterally. Thus, system 100 solves the need in the art for an apparatus that more easily configures mobile fluoroscopy C-arm systems or other mobile imaging systems for lateral movement and yet will accommodate large main wheels while not requiring a greater width of the imaging system 100.

Some embodiments of system 100 also include one or more castered wheel(s) 108 mounted on the base 102. The castered wheel(s) 108 are mounted forward of the plurality of main wheels 104.

While the system 100 is not limited to any particular base 102, main wheels 104 and secondary wheel(s) 106 for sake of clarity a simplified base 102, main wheels 104 and secondary wheel(s) 106 are described.

Apparatus Embodiments

In the previous section, a system level overview of the operation of an embodiment was described. In this section, the particular apparatus of such an embodiment are described by reference to a series of diagrams.

Figure 2:
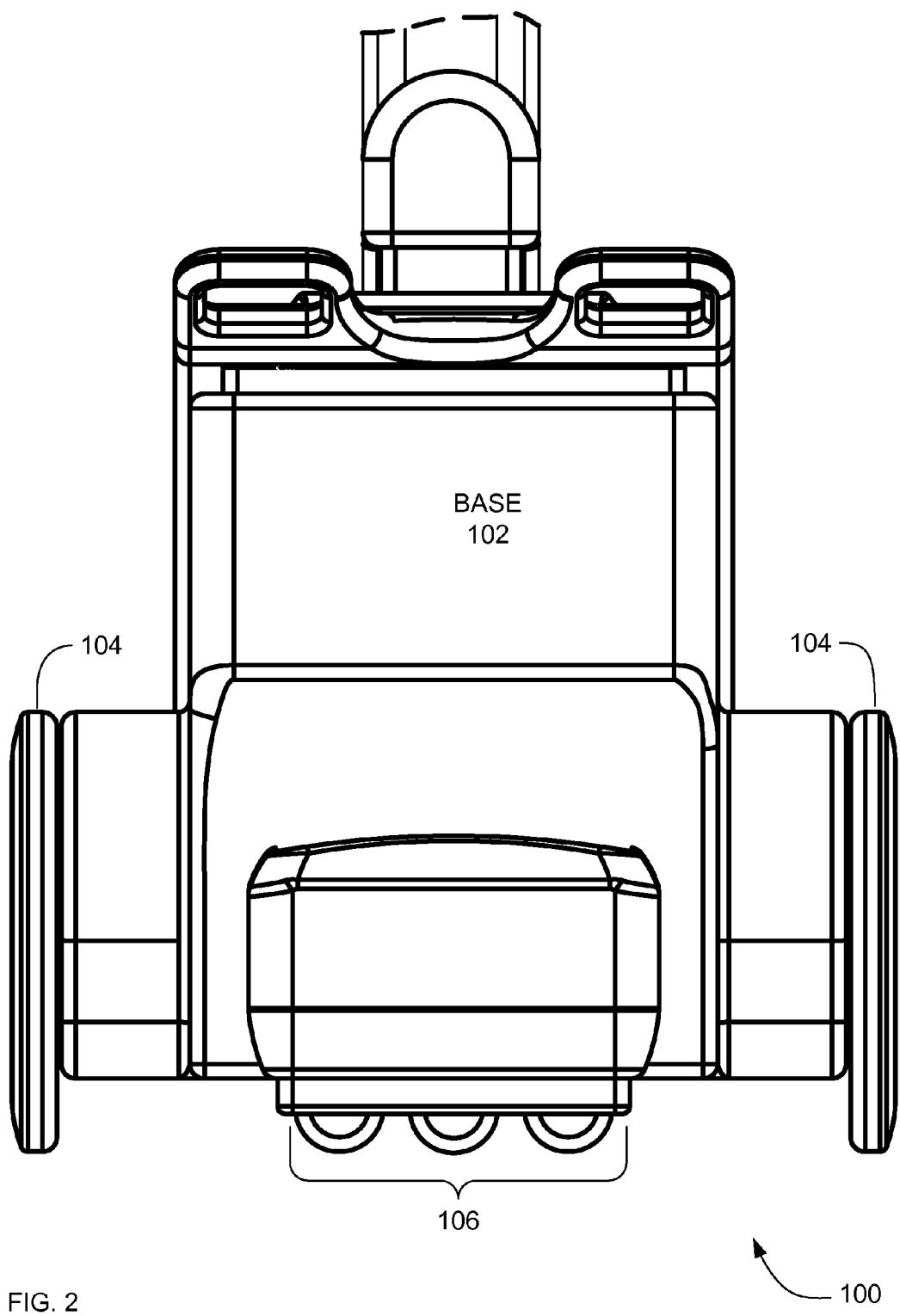
FIG. 2 is an enlarged rear-view diagram of a portion of a system to image objects, according to an embodiment.

FIG. 2 is an enlarged rear-view diagram of a portion of system 100 to image objects, according to an embodiment. System 100 solves the need in the art for an apparatus that configures a mobile imaging system for lateral movement and yet will accommodate large main wheels while not requiring a greater width of the mobile imaging system.

System 100 includes a base 102 and a plurality of main wheels 104 mounted on the base 102. System 100 also includes one or more secondary wheel(s) 106. The secondary wheel(s) 106 are mounted on the base 102.

The secondary wheel(s) 106 shown in FIG. 2 are in-line. In-line is aligned along a single line. FIG. 1 shows only one in-line array of secondary wheel(s) 106, however, system 100 is not limited by in-line or singular arrays of secondary wheel(s) 106. Other variations are within contemplation, such as a single pair of secondary wheel(s) 106 are mounted side-by-side (not in-line) or a plurality of in-line secondary wheel(s) 106.

The secondary wheel(s) 106 shown in FIG. 2 include three wheels. However, other embodiments of the secondary wheel(s) 106 that are not shown include any number of wheels, such as one wheel, two wheels, four wheels, five wheels or six wheels.

Secondary wheel(s) 106 provide a means to configure the system 100 to be moved laterally. Thus, system 100 solves the need in the art for an apparatus that more easily configures mobile fluoroscopy C-arm systems or other mobile imaging systems for lateral movement and yet will accommodate large main wheels while not requiring a greater width of the imaging system 100.

Figure 3:
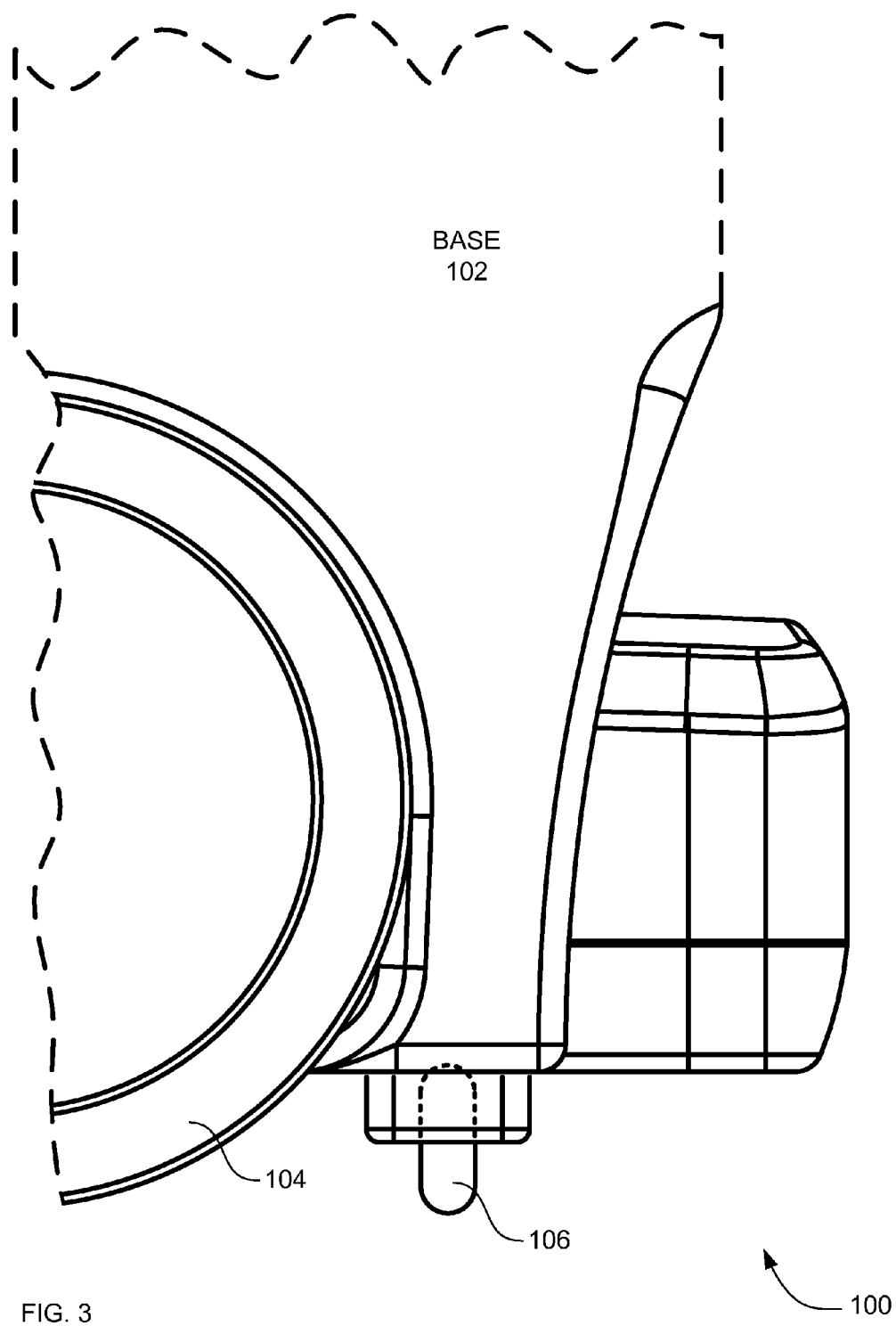
FIG. 3 is an enlarged side-view diagram of a portion of a system to image objects, according to an embodiment.

FIG. 3 is an enlarged side-view diagram of a portion of system 100 to image objects, according to an embodiment. The enlarged side-view shows the area in the vicinity of the secondary wheel(s).

System 100 includes a base 102 and a plurality of main wheels 104 mounted on the base 102. System 100 also includes one or more secondary wheel(s) 106. The secondary wheel(s) 106 are mounted on the base 102.

The secondary wheel(s) 106 shown in FIG. 3 are in-line, aligned along a single line. FIG. 1 shows only one in-line array of secondary wheel(s) 106, however, system 100 is not limited by in-line or singular arrays of secondary wheel(s) 106. Other variations are within contemplation, such as a single pair of secondary wheel(s) 106 that are mounted side-by-side (not in-line) or a plurality of in-line secondary wheel(s) 106.

System 100 solves the need in the art for an apparatus that configures a mobile imaging system for lateral movement and yet will accommodate large main wheels while not requiring a greater width of the mobile imaging system.

Figure 4:
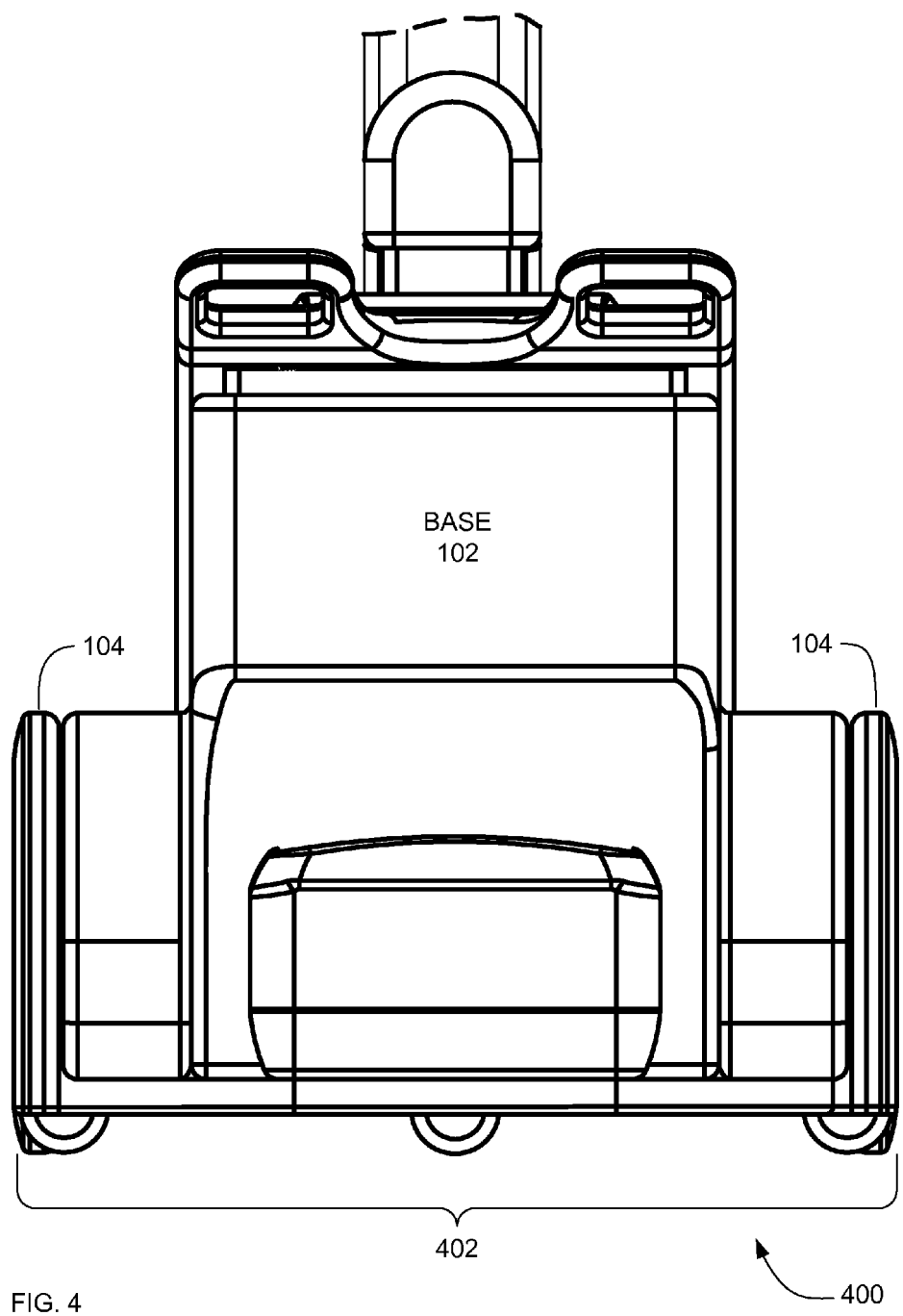
FIG. 4 is an enlarged rear-view diagram of a portion of a system to image objects, having secondary wheel(s) spanning the width of a base, according to an embodiment.

FIG. 4 is an enlarged rear-view diagram of a portion of a system 400 to image objects, having secondary wheel(s) spanning the width of a base 102, according to an embodiment. System 400 solves the need in the art for an apparatus that configures a mobile imaging system for lateral movement and yet will accommodate large main wheels while not requiring a greater width of the mobile imaging system.

System 400 includes a base 102 and a plurality of main wheels 104 mounted on the base 102. System 400 also includes one or more secondary wheel(s) 402. The secondary wheel(s) 402 are mounted on the base 102.

The plurality of secondary wheels 402 span about the lateral distance of the plurality of main wheels 104.

Figure 5:
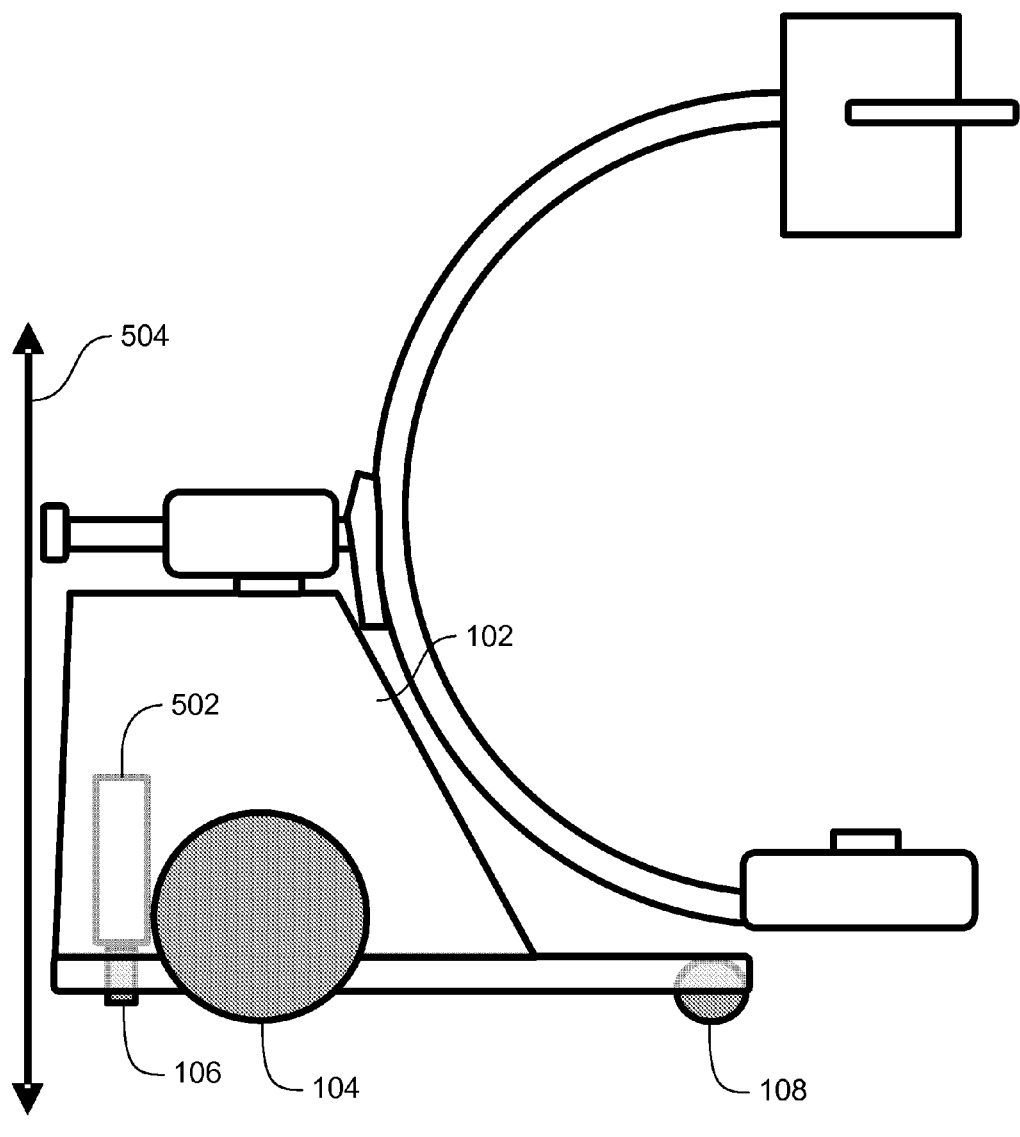
FIG. 5 is a cross section side-view block diagram of an apparatus to image an object that includes a carriage mechanism in a retracted position, according to an embodiment.

FIG. 5 is a cross section side-view block diagram of apparatus 500 to image an object that includes a carriage mechanism in a retracted position, according to an embodiment. Apparatus 500 solves the need in the art for an apparatus that configures a mobile imaging system for lateral movement and yet will accommodate large main wheels while not requiring a greater width of the mobile imaging system.

Apparatus 500 includes a carriage mechanism 502. The carriage mechanism 502 is operably coupled to the secondary wheel(s) 106. The carriage mechanism 502 is operable to move the secondary wheel(s) 106 along a vertical axis 504 of the apparatus 500. In the mode shown in the apparatus 500, the carriage mechanism has retracted the secondary wheel(s) 106. The motion along the vertical axis 504 extends upward to the extent that the secondary wheel(s) 106 can extend above the main wheels 104 such that no weight is placed on the secondary wheel(s) 106.

Figure 6:
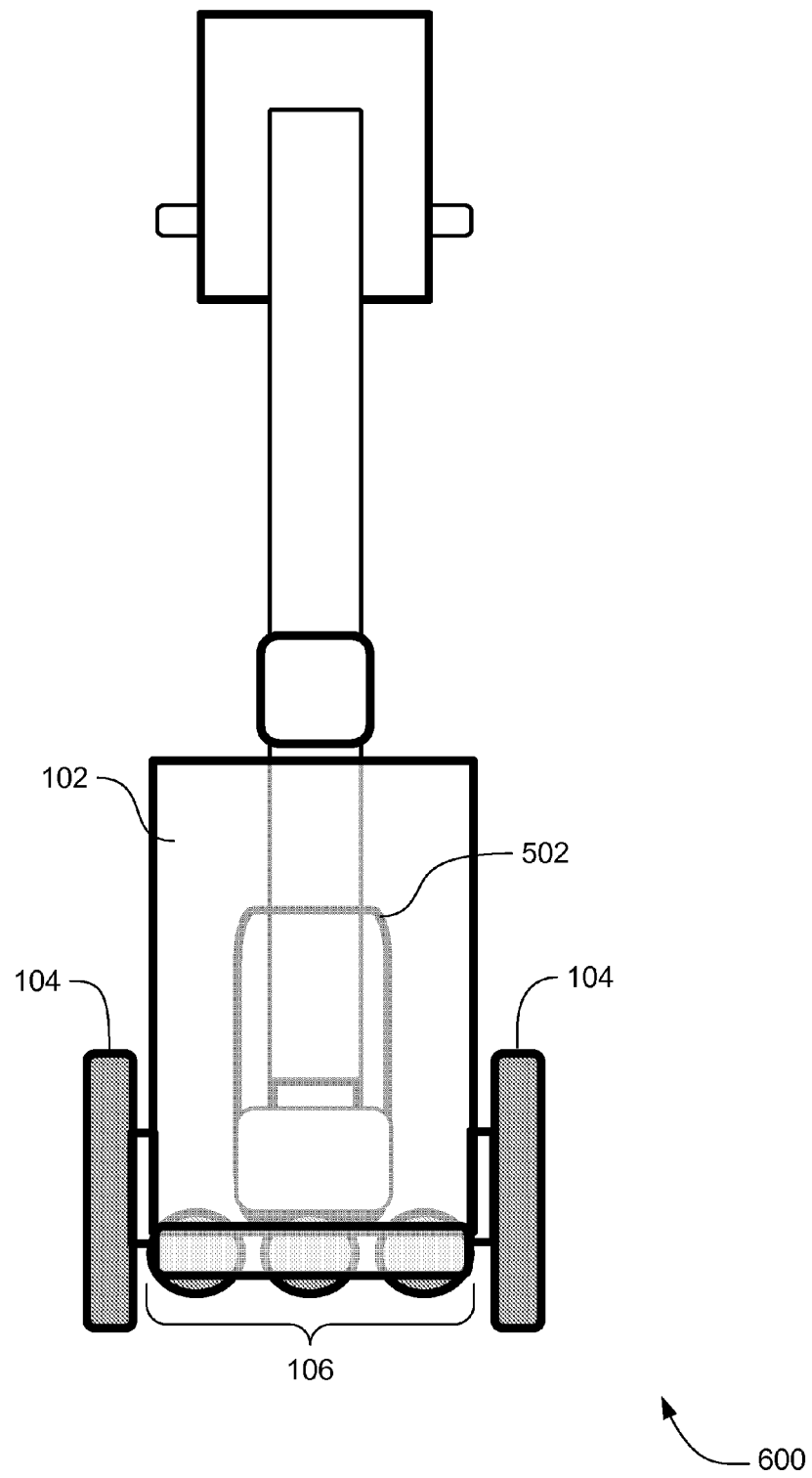
FIG. 6 is a cross section rear-view block diagram of an apparatus to image an object that includes a carriage mechanism in a retracted position, according to an embodiment.

FIG. 6 is a cross section rear-view block diagram of apparatus 600 to image an object that includes a carriage mechanism in a retracted position, according to an embodiment.

Figure 7:
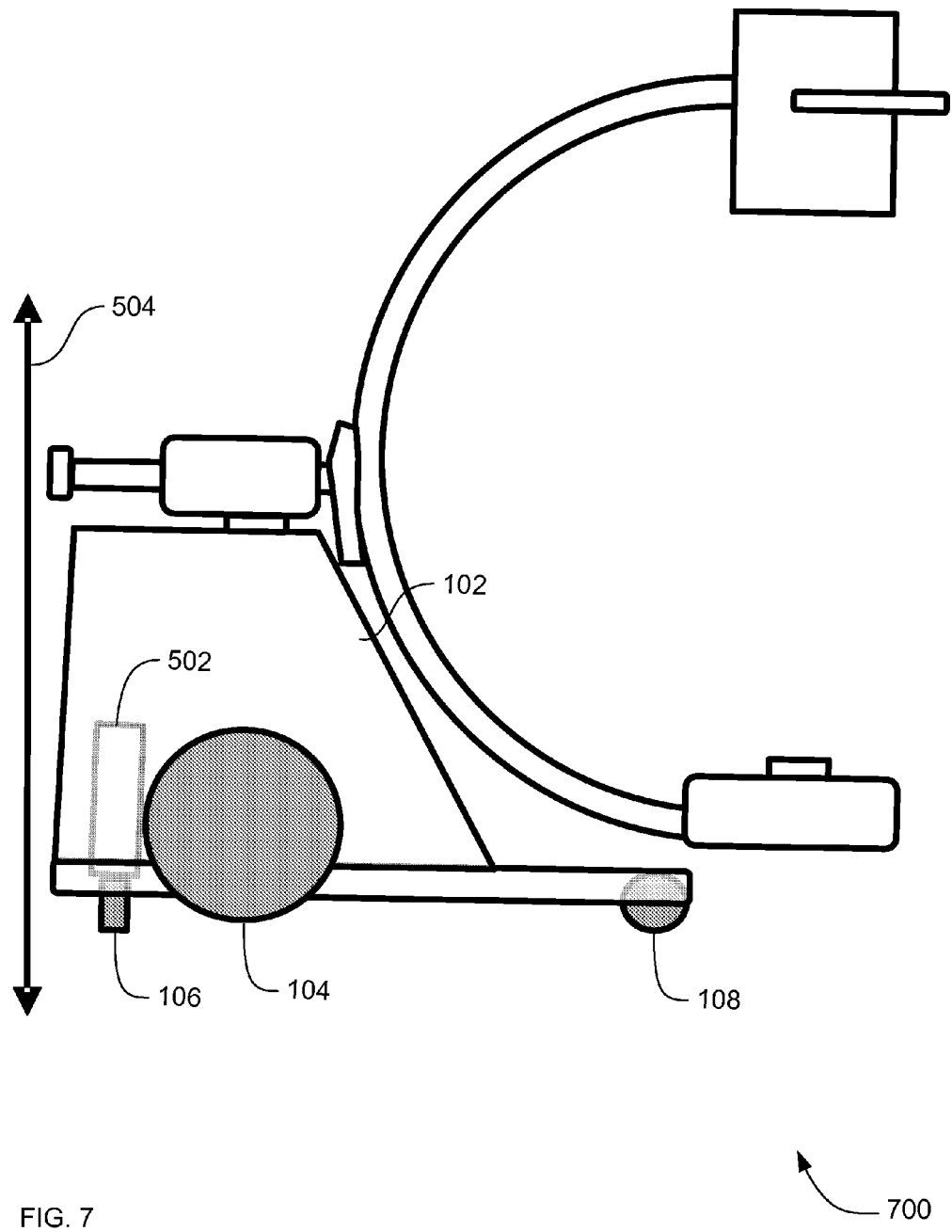
FIG. 7 is a cross section side-view block diagram of an apparatus to image an object that includes a carriage mechanism in an extended position, according to an embodiment.

FIG. 7 is a cross section side-view block diagram of apparatus 700 to image an object that includes a carriage mechanism in an extended position, according to an embodiment. In FIG. 7, the motion along the vertical axis 504 extends downward to the extent that the secondary wheel(s) 106 extend below the main wheels 104 such that no weight is placed on the main wheels 104.

Figure 8:
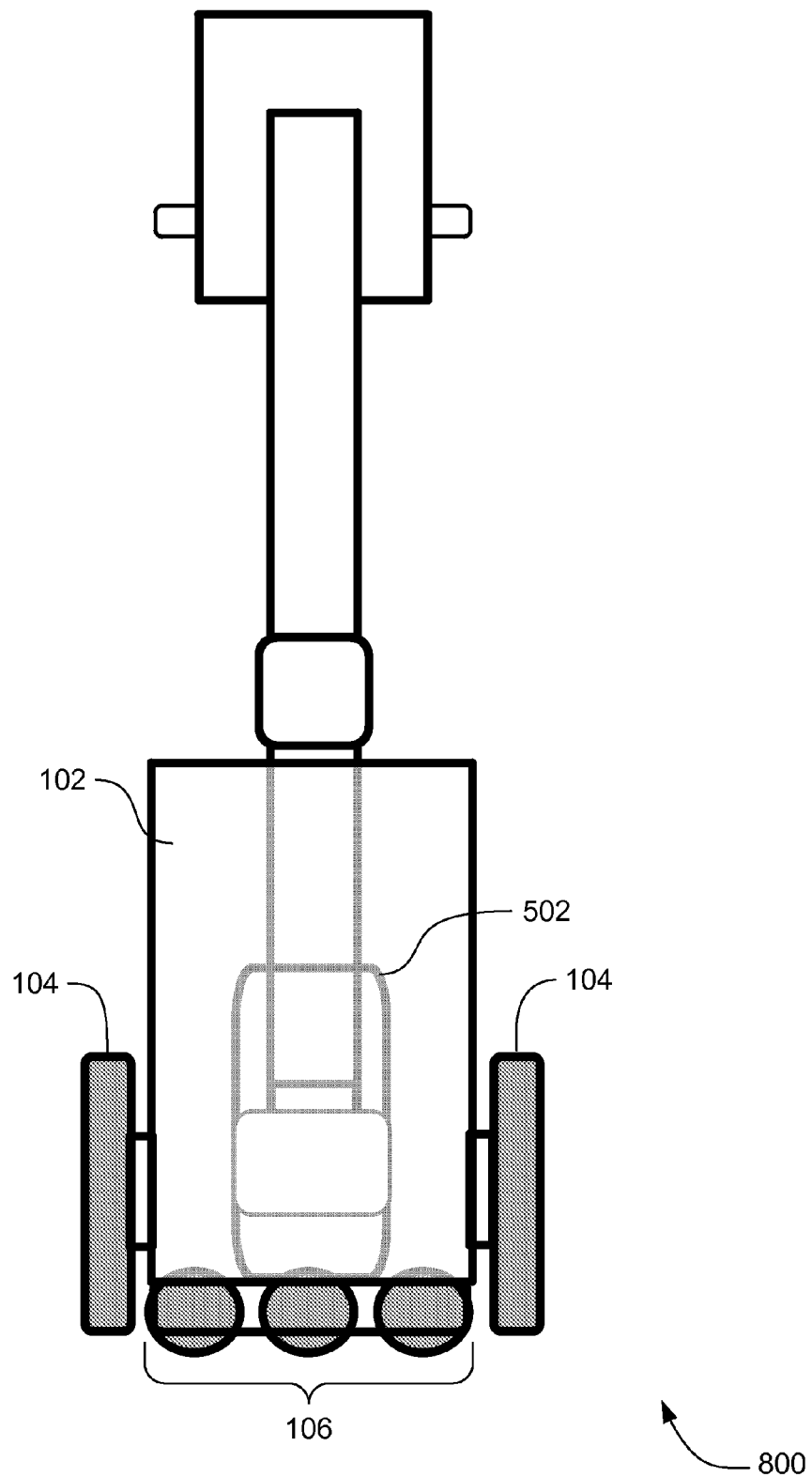
FIG. 8 is a cross section rear-view block diagram of an apparatus to image an object that includes a carriage mechanism in an extended position, according to an embodiment.

FIG. 8 is a cross section rear-view block diagram of apparatus 800 to image an object that includes a carriage mechanism in an extended position, according to an embodiment.

Figure 9:
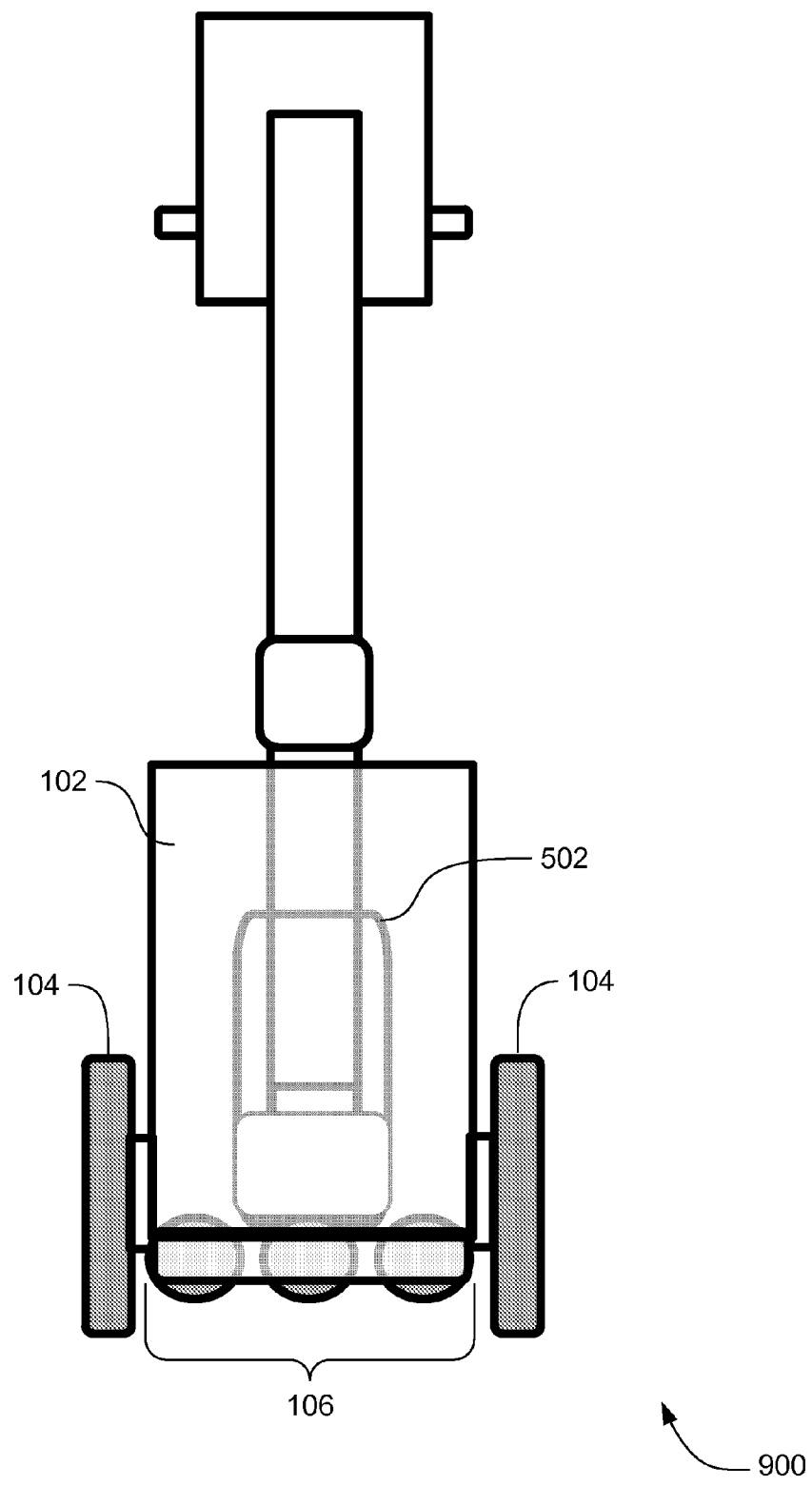
FIG. 9 is a cross section rear-view block diagram of an apparatus to image an object that includes a carriage mechanism in a retracted position, according to an embodiment.

FIG. 9 is a cross section rear-view block diagram of apparatus 900 to image an object that includes a carriage mechanism in a retracted position, according to an embodiment.

Figure 10:
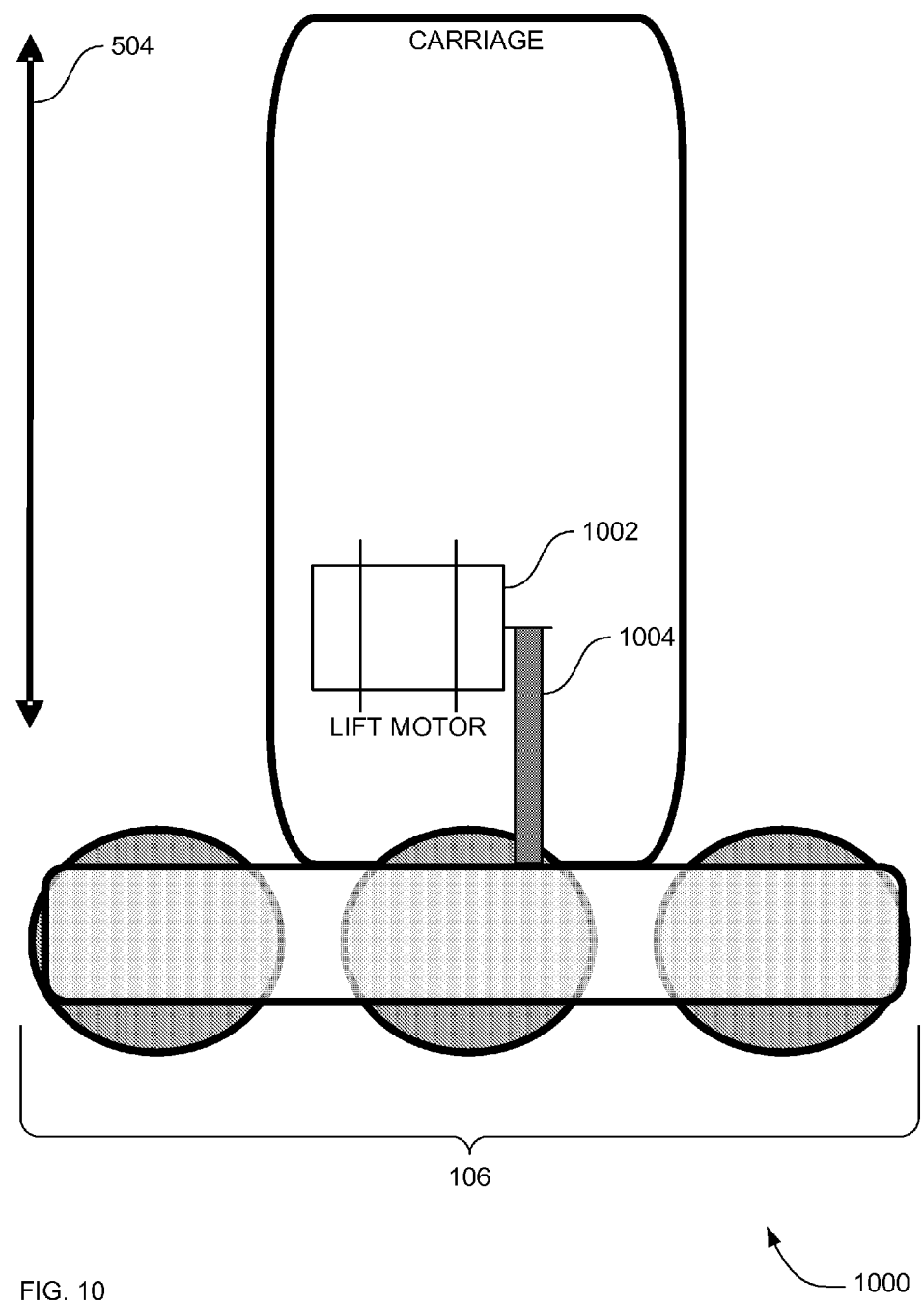
FIG. 10 is a cross section block diagram of a carriage mechanism for secondary wheel(s) on a mobile imaging device that includes a lift motor, according to an embodiment.

FIG. 10 is a cross section block diagram of carriage mechanism 1000 for secondary wheel(s) on a mobile imaging device that includes a lift motor, according to an embodiment. Carriage mechanism 1000 is one embodiment of carriage mechanism 502 in the above figures.

Carriage mechanism 1000 includes a lift motor 1002. The lift motor 1002 is operably coupled to the secondary wheel(s) 106, such as through a belt 1004. The lift motor 1002 is operable to move the secondary wheel(s) 106 along the vertical axis 504 of the mobile imaging device. Alternative devices to the lift motor 1002 that are operable to move the secondary wheel(s) 106 include a gas spring device and/or a pneumatic lift device.

Figure 11:
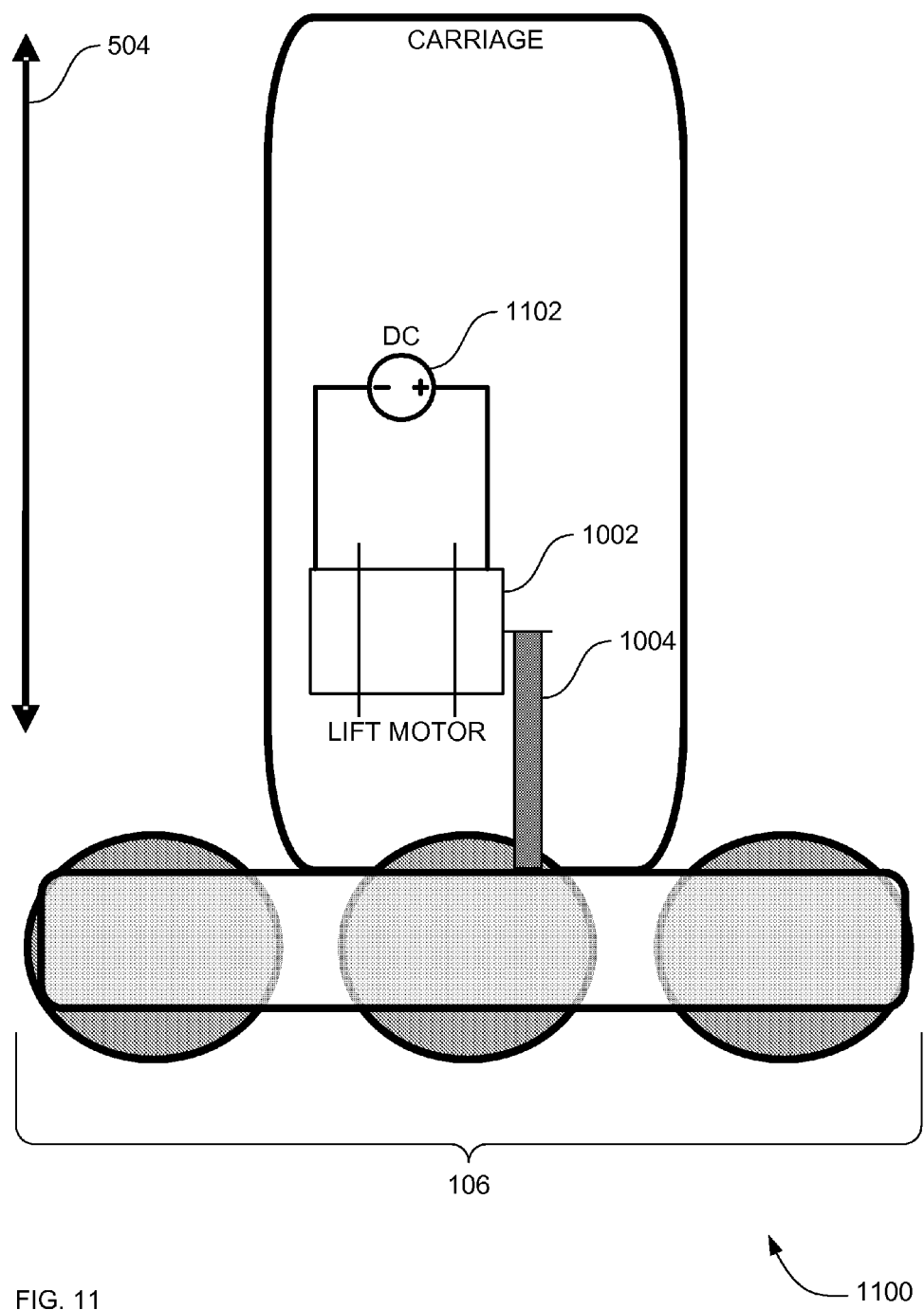
FIG. 11 is a cross section block diagram of a carriage mechanism for secondary wheel(s) on a mobile imaging device that includes a lift motor and a battery, according to an embodiment.

FIG. 11 is a cross section block diagram of carriage mechanism 1100 for secondary wheel(s) on a mobile imaging device that includes a lift motor and a battery, according to an embodiment. Carriage mechanism 1100 is one embodiment of carriage mechanism 502 and carriage mechanism 1000 in above figures. Carriage mechanism 1100 includes a battery 1102 that is operably coupled to the lift motor 1002.

Figure 12:
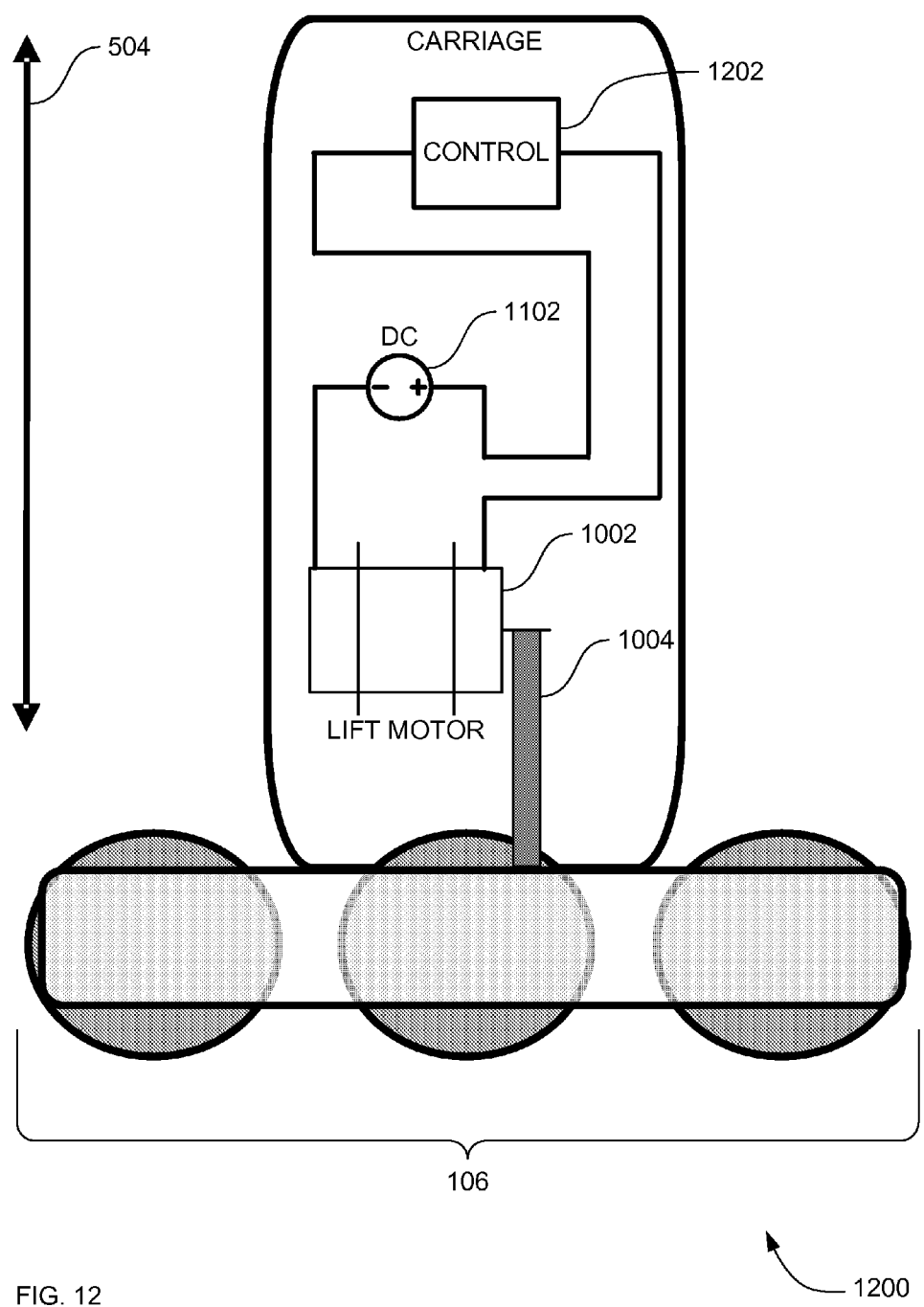
FIG. 12 is a cross section block diagram of a carriage mechanism for secondary wheel(s) on a mobile imaging device that includes a lift motor, a battery and control mechanism, according to an embodiment.

FIG. 12 is a cross section block diagram of carriage mechanism 1200 for secondary wheel(s) on a mobile imaging device that includes a lift motor, a battery and control mechanism, according to an embodiment. Carriage mechanism 1200 is one embodiment of carriage mechanisms 502, 1000 and 1100 in above figures. Carriage mechanism 1200 includes a control mechanism 1202. The control mechanism 1202 is operably coupled to, or is a part of, the carriage mechanism, to actuate and control the carriage mechanism in movement of the secondary wheel(s) 106.

Figure 13:
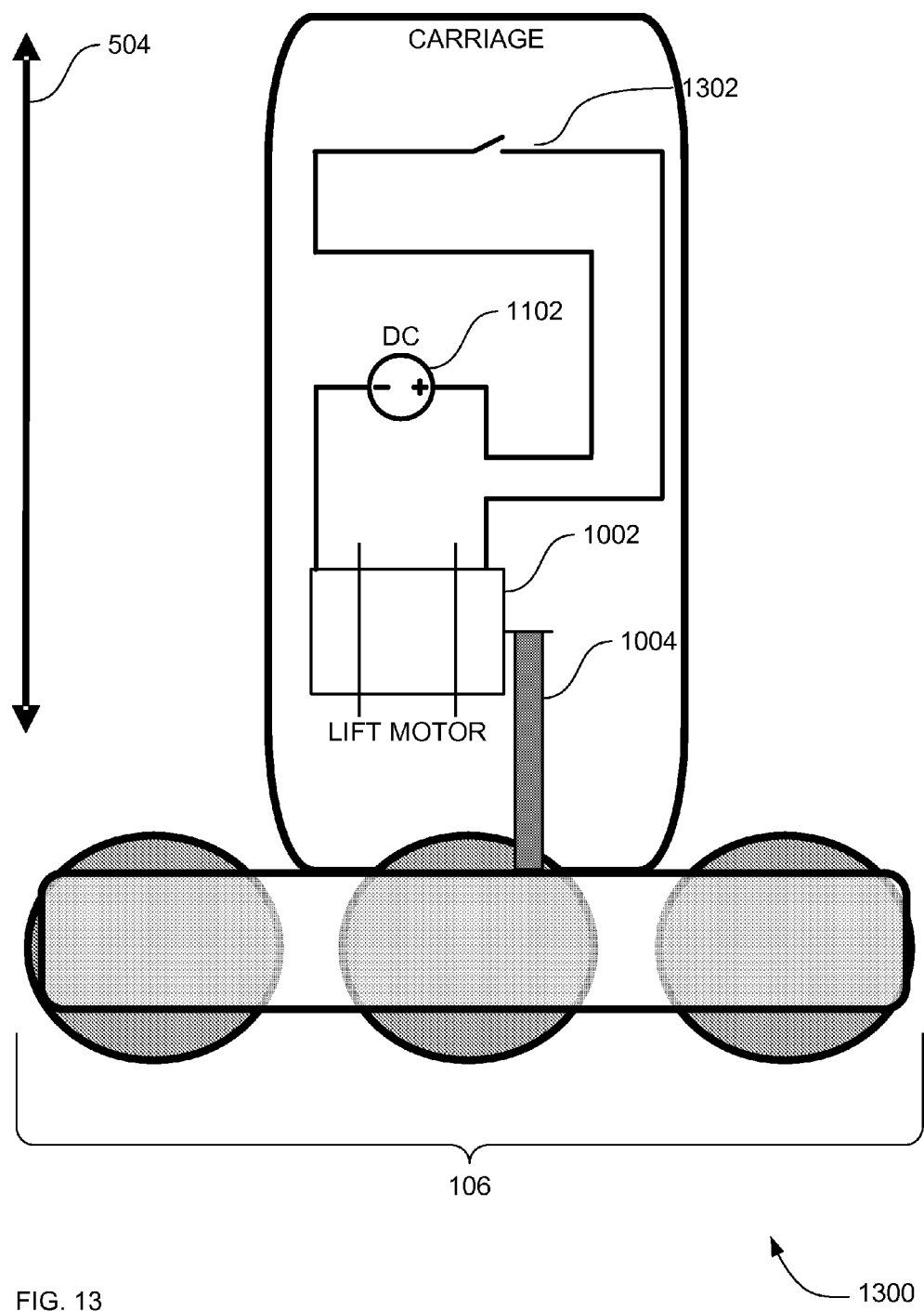
FIG. 13 is a cross section block diagram of a carriage mechanism for secondary wheel(s) on a mobile imaging device that includes a lift motor, a battery and activate/deactivate switch, according to an embodiment.

FIG. 13 is a cross section block diagram of carriage mechanism 1300 for secondary wheel(s) on a mobile imaging device that includes a lift motor, a battery and activate/deactivate switch, according to an embodiment. Carriage mechanism 1300 is one embodiment of carriage mechanisms 502, 1000 and 1100 in above figures. Carriage mechanism 1300 includes an activate/deactivate switch 1302. The activate/deactivate switch 1302 is operably coupled to, or is a part of, the carriage mechanism to actuate and control the carriage mechanism in movement of the secondary wheel(s) 106.

Figure 14:
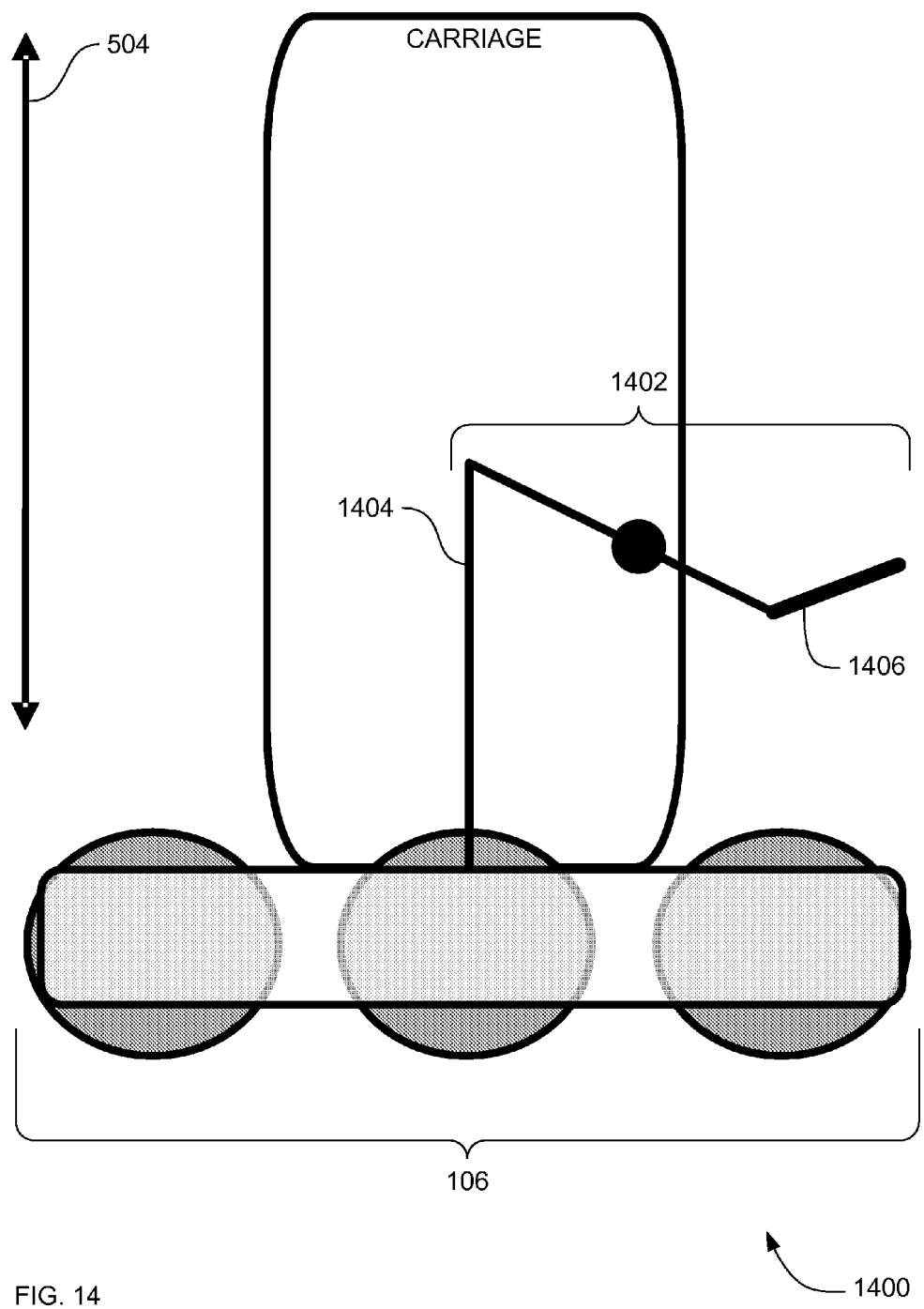
FIG. 14 is a cross section block diagram of a carriage mechanism for secondary wheel(s) on a mobile imaging device that includes a mechanical levering device, according to an embodiment.

FIG. 14 is a cross section block diagram of a carriage mechanism 1400 for secondary wheel(s) on a mobile imaging device that includes a mechanical levering device, according to an embodiment. Carriage mechanism 1100 is one embodiment of carriage mechanism 502 in above figures. Apparatus 1400 includes a mechanical levering device 1402 (e.g. a manual jack 1404 with foot pedal 1406) that is operably coupled to the secondary wheel(s) 106. The mechanical levering device 1402 is operable to move the secondary wheel(s) 106 along a vertical axis 504 of the mobile imaging device.

In another embodiment, the manual jack 1404 is mounted to the base 102, that is operable to raise the weight of the C-arm system off of the forward facing rear, and transfer the weight to the secondary wheel(s) 106 for lateral motion. The jack relies on the weight and strength of the operator to apply the necessary leverage.

Figure 15:
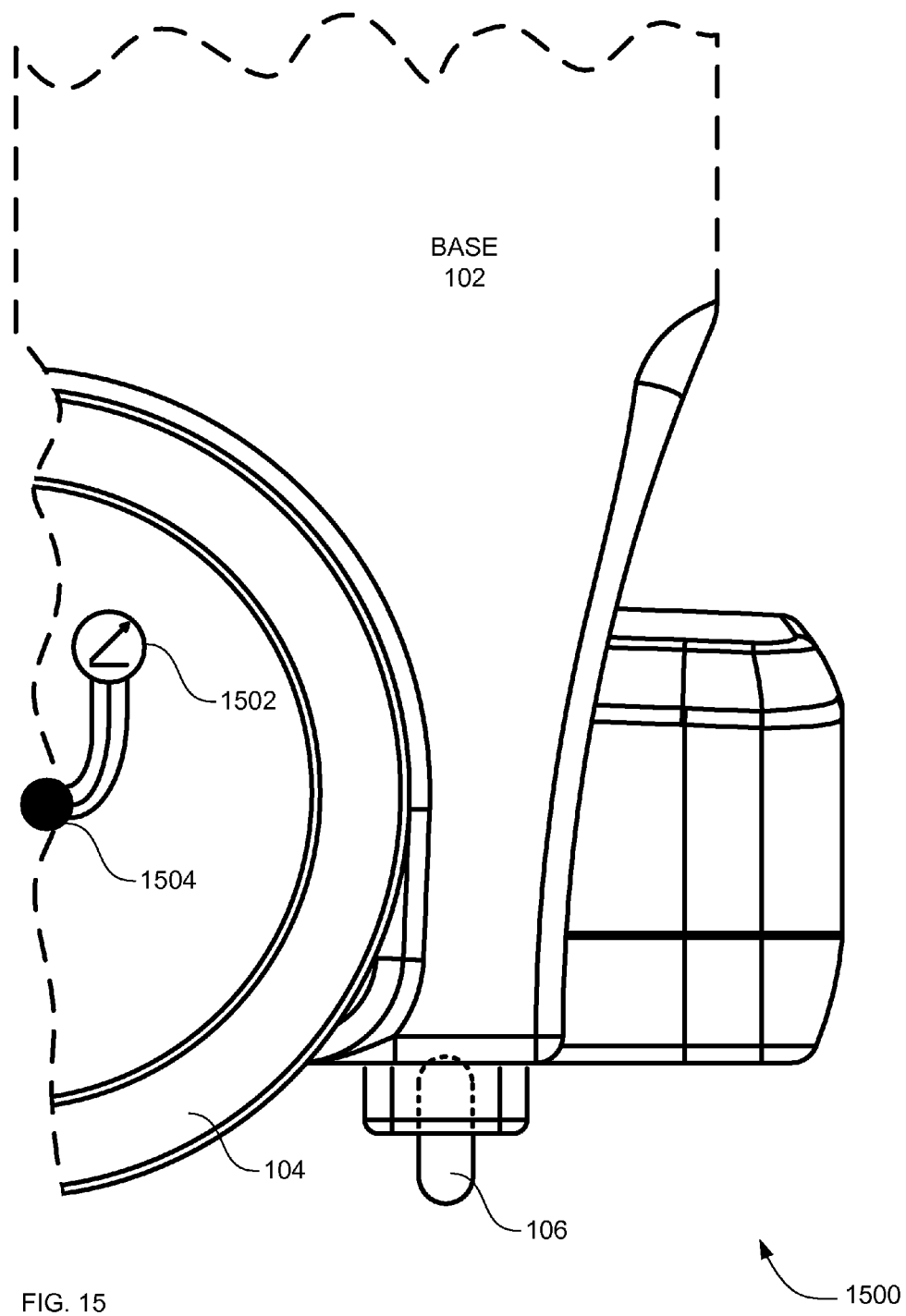
FIG. 15 is an enlarged side-view diagram of an apparatus to image objects that includes a load-sensing device, according to an embodiment.

FIG. 15 is an enlarged side-view block diagram of apparatus 1500 to image objects that includes a load-sensing device, according to an embodiment. The close-up side view shows the area in the vicinity of the secondary wheel(s).

Apparatus 1500 includes a base 102 and a plurality of main wheels 104 mounted on the base of the base 102. Apparatus 1500 also includes one or more secondary wheel(s) 106. The secondary wheel(s) 106 are mounted on the base 102.

Apparatus 1500 includes a sensor 1502. The sensor 1502 is operably coupled to an axle 1504 of the main wheels 104. The sensor 1502 determines the weight bearing down upon the plurality of main wheels 104.

Method Embodiments

In the previous section, apparatus of the operation of an embodiment was described. In this section, the particular methods performed by control mechanism 1202 of FIG. 12 of such an embodiment are described by reference to a series of flowcharts.

Figure 16:
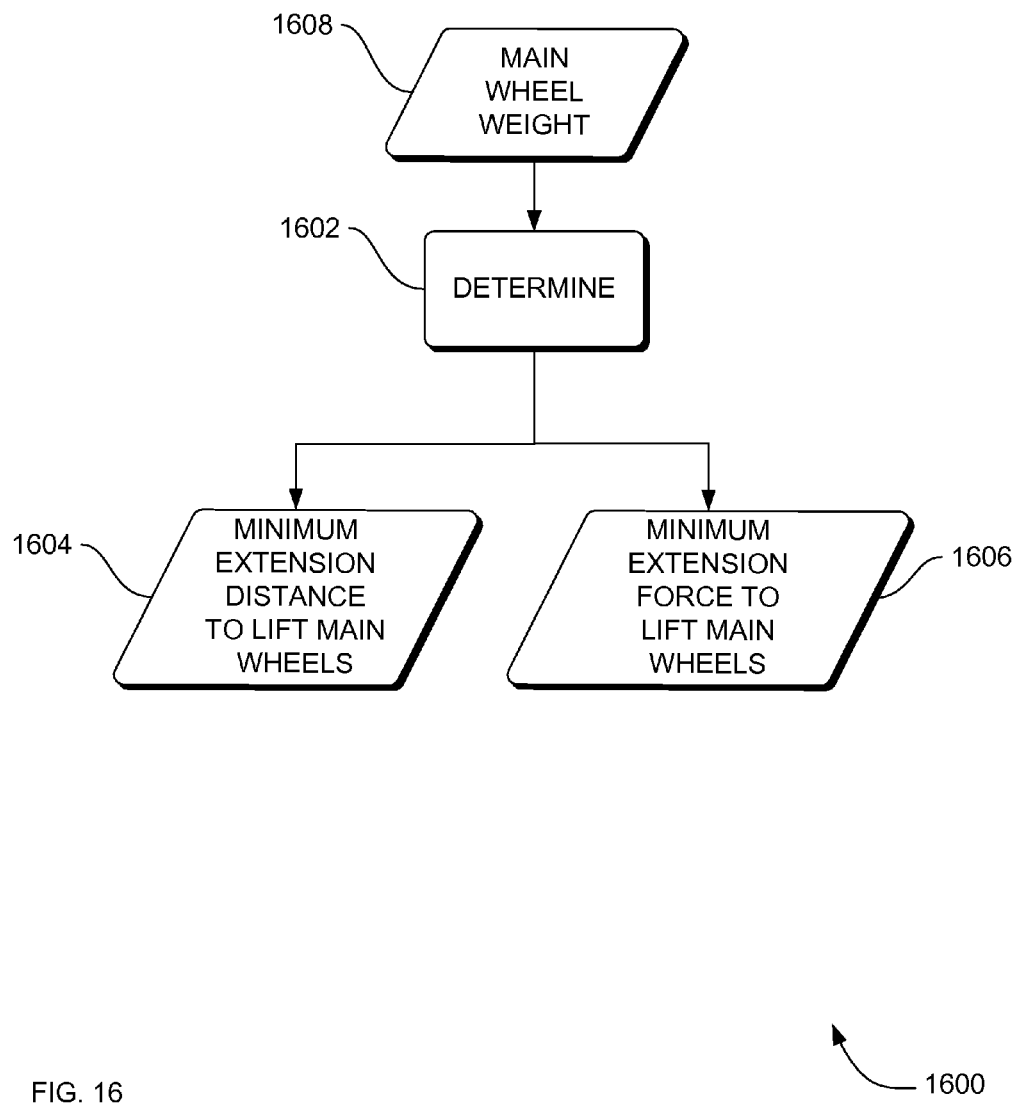
FIG. 16 is a flowchart of a method to determine extension of secondary wheel(s) according to an embodiment.

FIG. 16 is a flowchart of a method 1600 to determine extension of secondary wheel(s) according to an embodiment. Method 1600 includes determining 1602 a minimum distance 1604 and a minimum amount of force 1606 that the carriage mechanism needs to move the plurality of secondary wheels to the extent that the plurality of secondary wheels extend below the main wheels such that no weight is placed on the main wheels. The determination 1602 is made in reference to the weight 1608 determined by the sensor.

Figure 17:
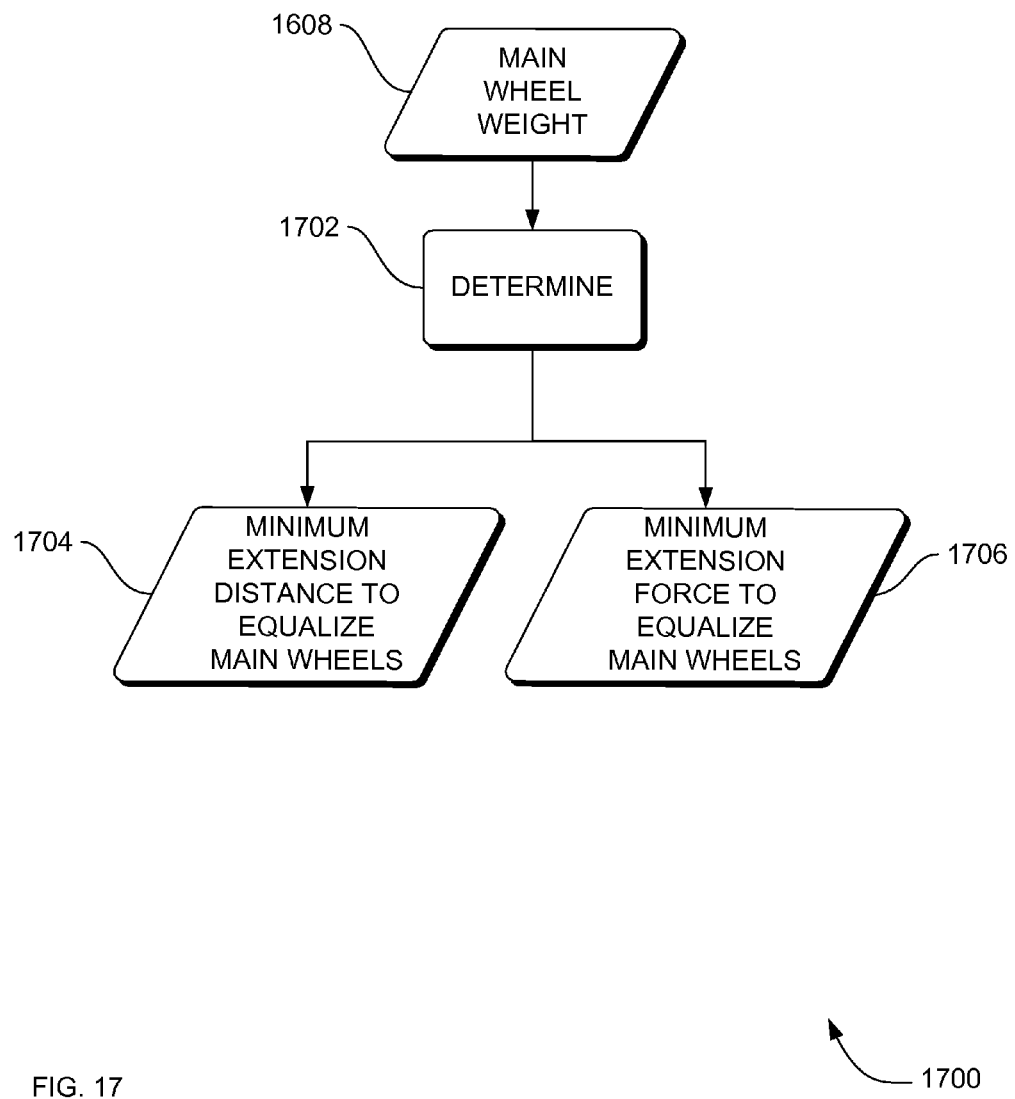
FIG. 17 is a flowchart of a method to determine extension of secondary wheel(s) according to an embodiment.

FIG. 17 is a flowchart of a method 1700 to determine extension of secondary wheel(s) according to an embodiment. Method 1700 includes determining 1702 a minimum distance 1704 and a minimum amount of force 1706 that the carriage mechanism needs to move the plurality of secondary wheels to the extent that the plurality of secondary wheels extend below the main wheels such that about equal weight is placed on the main wheels as the weight place on the plurality of secondary wheels. The determination 1702 is made in reference to the weight 1608 determined by the sensor.

In some embodiments, methods 1600-1700 are implemented as a computer data signal embodied in a carrier wave, that represents a sequence of instructions which, when executed by a processor cause the processor to perform the respective method. In other embodiments, methods 1600-1700 are implemented as a computer-accessible medium having executable instructions capable of directing a processor, to perform the respective method. In varying embodiments, the medium is a magnetic medium, an electronic medium, or an optical medium.

A wide variety of computer hardware and computing environments are suitable to implement the control mechanism. Some embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment. The computer hardware includes a processor that is commercially available from Intel, Motorola, Cyrix and others. The computer hardware also includes random-access memory (RAM), read-only memory (ROM), and optionally one or more mass storage devices. The memory and mass storage devices are types of computer-accessible media. The processor executes computer programs stored on the computer-accessible media.

CONCLUSION

An imaging device with lateral wheels is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in any other configuration that provides the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future imaging devices, different control mechanism, and new wheels.

The terminology used in this application is meant to include all microprocessor and imaging environments and alternate technologies which provide the same functionality as described herein

We claim:

1. An apparatus to image objects, the apparatus comprising:

a base;

a plurality of main wheels mounted on the base;

a sensor operably coupled to an axle of the plurality of main wheels to determine the weight bearing down upon the plurality of main wheels, at least one secondary wheel mounted on the base and mounted in a perpendicular direction to the main wheels; and a carriage mechanism operably coupled to the at least one secondary wheel and operable to move the at least one secondary wheel along a vertical axis of the apparatus, the motion along the vertical axis extending downward to the extent that the at least one secondary wheel can extend below the main wheels such that no weight is placed on the main wheels and the motion along the vertical axis extending upward to the extent that the at least one secondary wheel can extend above the main wheels such that no weight is placed on the at least one secondary wheel;

a control mechanism operably coupled to the carriage mechanism to actuate and control the carriage mechanism in movement of the at least one secondary wheel, wherein the control mechanism is further operable to determine in reference to the weight determined by the sensor, a minimum distance and a minimum amount of force that the carriage mechanism needs to move the at least one secondary wheel to the extent that the at least one secondary wheel extends below the main wheels such that no weight is placed on the main wheels.

2. The apparatus of claim 1, wherein the at least one secondary wheel further comprise:
a plurality of in-line wheels.

3. The apparatus of claim 2, wherein the plurality of in-line wheels further comprise:
a range of between two and six in-line wheels.

4. The apparatus of claim 1, wherein the at least one secondary wheel further comprises:
at least one secondary wheel that spans about the lateral distance of the plurality of main wheels.

5. The apparatus of claim 1, wherein the at least one secondary wheel mounted on the base further comprises:
a plurality of secondary wheels that span about a lateral distance of the plurality of main wheels.

6. The apparatus of claim 1, further comprising:
a plurality of castered wheels mounted on the base and mounted forward of the plurality of main wheels.

7. The apparatus of claim 1, wherein the at least one secondary wheel further comprises:
a single pair of secondary wheels that are mounted side-by-side and not in-line.

8. The apparatus of claim 7, wherein the carriage mechanism further comprises:
a lift motor operably coupled to the at least one secondary wheel and operable to move the at least one secondary wheel along the vertical axis of the apparatus.

9. The apparatus of claim 8, wherein the carriage mechanism further comprises:
a battery operably coupled to the lift motor.

10. The apparatus of claim 7,
wherein the control mechanism is a part of the carriage mechanism.

11. The apparatus of claim 1, wherein the control mechanism further comprises:
an activate/deactivate switch that is operably coupled to the carriage mechanism to actuate and control the carriage mechanism in movement of the at least one secondary wheel.

12. The apparatus of claim 1, further comprising:
not having a lock on the main wheels.

13. The apparatus of claim 12, wherein the control mechanism further comprises:
a computer executing computer-executable instructions.

14. The apparatus of claim 12, wherein the control mechanism is further operable to determine in reference to the weight determined by the sensor, a minimum distance and a minimum amount of force that the carriage mechanism needs to move the at least one secondary wheel to the extent that the at least one secondary wheel extends below the main wheels such that about equal weight is placed on the main wheels as the weight that is placed on the at least one secondary wheel.

15. The apparatus of claim 1, wherein the at least one secondary wheel further comprises:
a plurality of secondary wheels mounted rearward of the plurality of main wheels.

16. The apparatus of claim 1, further comprising:
a mobile fluoroscopy C-arm system.

17. The apparatus of claim 1, wherein the control mechanism is further operable to determine a minimum distance that the carriage mechanism needs to move the at least one secondary wheel to the extent that about equal weight is placed on the main wheels and the secondary wheels.

18. A mobile imaging system comprising:
a base;
a plurality of main wheels mounted on the base;
a sensor operably coupled to an axle of the plurality of main wheels to determine the weight bearing down upon the plurality of main wheels;
a plurality of castered wheels mounted on the base and mounted forward of the plurality of main wheels;
a plurality of lateral wheels mounted on the base and mounted rearward of the plurality of main wheels and mounted in a perpendicular direction to the main wheels;
a lift motor operably coupled to the plurality of lateral wheels and operable to move the plurality of the lateral wheels along a vertical axis of the mobile imaging system; and
a control mechanism operably coupled to the lift motor to actuate and control the lift motor in movement of the lateral wheels,
wherein the control mechanism is further operable to determine in reference to the weight determined by the sensor, a minimum distance and a minimum amount of force that the lateral wheels need to move to the extent that the lateral wheels extend below the main wheels such that no weight is placed on the main wheels.

19. The mobile imaging system of claim 18, wherein the control mechanism further comprises:
an activate/deactivate switch that is operably coupled to the carriage mechanism to actuate and control the carriage mechanism in movement of the lateral wheels.

20. The mobile imaging system of claim 18 further comprising:
at least one wheel mounted rearward of the plurality of main wheels and mounted in the same direction as the plurality of main wheels.

21. The mobile imaging system of claim 18, wherein the plurality of lateral wheels further comprise:
a range of between five and six lateral wheels.

22. The mobile imaging system of claim 18 wherein the control mechanism is further operable to determine a minimum distance that the carriage mechanism needs to move the lateral wheels to the extent that about equal weight is placed on the main wheels and the lateral wheels.

23. A mobile fluoroscopy C-arm system comprising:
a base;
a plurality of main wheels mounted on the base;
a sensor operably coupled to an axle of the plurality of main wheels to determine the weight bearing down upon the plurality of main wheels;
a plurality of castered wheels mounted on the base and mounted forward of the plurality of main wheels;

a plurality of lateral wheels mounted on the base and mounted rearward of the plurality of main wheels and mounted in a perpendicular direction to the main wheels;

a lift motor operably coupled to the plurality of lateral wheels and operable to move the plurality of the lateral wheels along a vertical axis of the mobile fluoroscopy C-arm system; and a control mechanism operably coupled to the lift motor to actuate and control the lift motor in movement of the lateral wheels, wherein the control mechanism further comprises an activate/deactivate switch that is operably coupled to the carriage mechanism to actuate and control the carriage mechanism in movement of the lateral wheels, wherein the control mechanism is further operable to determine in reference to the weight determined by the sensor, a minimum distance and a minimum amount of force that the carriage mechanism needs to move the at least one secondary wheel to the extent that the at least one secondary wheel extends below the main wheels such that about equal weight is placed on the main wheels as the weight that is placed on the at least one secondary wheel.

24. The mobile fluoroscopy C-arm system of claim 23 further comprising:

at least one wheel mounted rearward of the plurality of main wheels and mounted in the same direction as the plurality of main wheels.

25. The mobile fluoroscopy C-arm system of claim 23, wherein the plurality of lateral wheels further comprise:

a range of between five and six in-line wheels.

* * * * *